(12) United States Patent
Day

(10) Patent No.: US 8,816,866 B2
(45) Date of Patent: Aug. 26, 2014

(54) SONIC DETECTION OF FLOW STATE CHANGE FOR MEASUREMENT STATIONS

(75) Inventor: Donald Day, Cypress, TX (US)

(73) Assignee: Daniel Measurement & Control, Inc., Houston, TX (US)

( * ) Notice: Subject to any disclaimer, the term of this patent is extended or adjusted under 35 U.S.C. 154(b) by 505 days.

(21) Appl. No.: 12/988,287

(22) PCT Filed: Nov. 10, 2008

(86) PCT No.: PCT/US2008/083030
§ 371 (c)(1),
(2), (4) Date: Oct. 15, 2010

(87) PCT Pub. No.: WO2009/128864
PCT Pub. Date: Oct. 22, 2009

(65) Prior Publication Data
US 2011/0037598 A1    Feb. 17, 2011

Related U.S. Application Data

(60) Provisional application No. 61/045,794, filed on Apr. 17, 2008.

(51) Int. Cl.
*G01F 1/00* (2006.01)
*G01F 1/74* (2006.01)
*G01F 1/36* (2006.01)
*G01F 1/66* (2006.01)
*G01G 1/00* (2006.01)
*G01F 1/708* (2006.01)

(52) U.S. Cl.
CPC .. *G01F 1/36* (2013.01); *G01F 1/66* (2013.01); *G01G 1/00* (2013.01); *G01F 1/666* (2013.01); *G01F 1/7082* (2013.01)

USPC .......... 340/606; 340/603; 340/618; 340/621; 340/657; 340/661

(58) Field of Classification Search
None
See application file for complete search history.

(56) References Cited

U.S. PATENT DOCUMENTS 4,710,163 A * 12/1987 Butterfield ..................... 604/65
5,191,795 A    3/1993 Fellingham et al.
(Continued)

FOREIGN PATENT DOCUMENTS

| CN | 1853088 A | 10/2006 |
|---|---|---|
| CN | 1853098 A | 10/2006 |
| WO | 96/14559 | 5/1996 |
| WO | 2005/010470 A2 | 2/2005 |

OTHER PUBLICATIONS

International Application No. PCT/US2008/083030 Search Report and Written Opinion dated Feb. 24, 2009.

(Continued)

*Primary Examiner* — Julie Lieu
(74) *Attorney, Agent, or Firm* — Conley Rose, P.C.

(57) ABSTRACT

A method for audibly detecting a fluid flow state change in a flow meter pipeline. The flow state change may be identified as an upset in the normal flow state. The upset may be corrected to improve the accuracy of the flow meter. A system includes acoustic sensors mounted in the flow meter pipeline, and a computer to collect audible data from the acoustic sensors and compare the audible data to a baseline to detect an upset in the normal fluid flow state.

18 Claims, 3 Drawing Sheets

(56) References Cited

U.S. PATENT DOCUMENTS

| | | | |
|---|---|---|---|
| 5,594,180 A | 1/1997 | Carpenter et al. | |
| 5,660,171 A * | 8/1997 | Kimm et al. | 128/204.23 |
| 5,741,980 A * | 4/1998 | Hill et al. | 73/861.04 |
| 6,453,247 B1 * | 9/2002 | Hunaidi | 702/51 |
| 6,668,619 B2 * | 12/2003 | Yang et al. | 73/40.5 R |
| 7,290,450 B2 * | 11/2007 | Brown et al. | 73/579 |
| 8,220,484 B2 * | 7/2012 | Howitt | 137/551 |
| 2002/0124633 A1 * | 9/2002 | Yang et al. | 73/40.5 R |
| 2003/0183022 A1 * | 10/2003 | Sapelnikov et al. | 73/865.8 |
| 2004/0211272 A1 * | 10/2004 | Aronstam et al. | 73/866.5 |
| 2007/0068225 A1 * | 3/2007 | Brown | 73/40.5 A |
| 2007/0279235 A1 * | 12/2007 | Davis et al. | 340/606 |
| 2012/0190964 A1 * | 7/2012 | Hyde et al. | 600/407 |

OTHER PUBLICATIONS

Daniel Measurement & Control Inc., "Office Action dated Apr. 19, 2012," Canadian App. No. 2,721,504.

Daniel Measurement & Control Inc., "Office Action dated Mar. 22, 2012," Chinese App. No. 200880128698.8.

Daniel Measurement & Control Inc., letter detailing "Office Action dated Nov. 5, 2011," Mexican App. No. MX/a/2010/011331.

* cited by examiner

SONIC DETECTION OF FLOW STATE CHANGE FOR MEASUREMENT STATIONS

CROSS-REFERENCE TO RELATED APPLICATION

This application is the U.S. National Stage under 35 U.S.C. §371 of International Patent Application No. PCT/US2008/083030 filed Nov. 10, 2008, which claims the benefit of U.S. Provisional Patent Application No. 61/045,794 filed Apr. 17, 2008, entitled "Sonic Detection of Flow State Change For Measurement Stations."

STATEMENT REGARDING FEDERALLY SPONSORED RESEARCH OR DEVELOPMENT

Not applicable.

BACKGROUND

After hydrocarbons have been removed from the ground, the fluid stream (such as crude oil or natural gas) is transported from place to place via pipelines. It is desirable to know with accuracy the amount of fluid flowing in the stream, and particular accuracy is demanded when the fluid is changing hands, or "custody transfer." Custody transfer can occur at a fluid fiscal transfer measurement station or skid, which may include key transfer components such as a measurement device or flow meter, a proving device, associated pipes and valves, and electrical controls. Measurement of the fluid stream flowing through the overall delivery pipeline system starts with the flow meter, which may include a turbine meter, a positive displacement meter, an ultrasonic meter, a coriolis meter or a vortex meter.

The fluid stream typically undergoes changes of pressure, temperature and flow rate. These changes are represented as changes in the flow characteristics, and affect accurate measurement of the product being delivered. Changing flow characteristics of the fluid stream are normally verified by the operator via the effects of the changes on the measurement device. This verification is conducted by proving the meter with a proving device, or prover in the case of liquid hydrocarbons. A calibrated prover, adjacent the measurement device on the skid and in fluid communication with the measurement device, is sampled and the sampled volumes are compared to the throughput volumes of the measurement device. If there are statistically important differences between the compared volumes, the throughput volume of the measurement device is adjusted to reflect the actual flowing volume as identified by the prover.

However, aside from the changes just described sensed by instrumentation, flow changes can manifest in other ways as well. Thus, the principles of the present disclosure are directed to overcoming one or more of the limitations of the existing processes for ensuring accuracy and reliability of the measurement station and custody transfer, and identifying maintenance issues.

BRIEF DESCRIPTION OF THE DRAWINGS

For a detailed description of exemplary embodiments, reference will now be made to the accompanying drawings in which.

DETAILED DESCRIPTION

Figure 1:
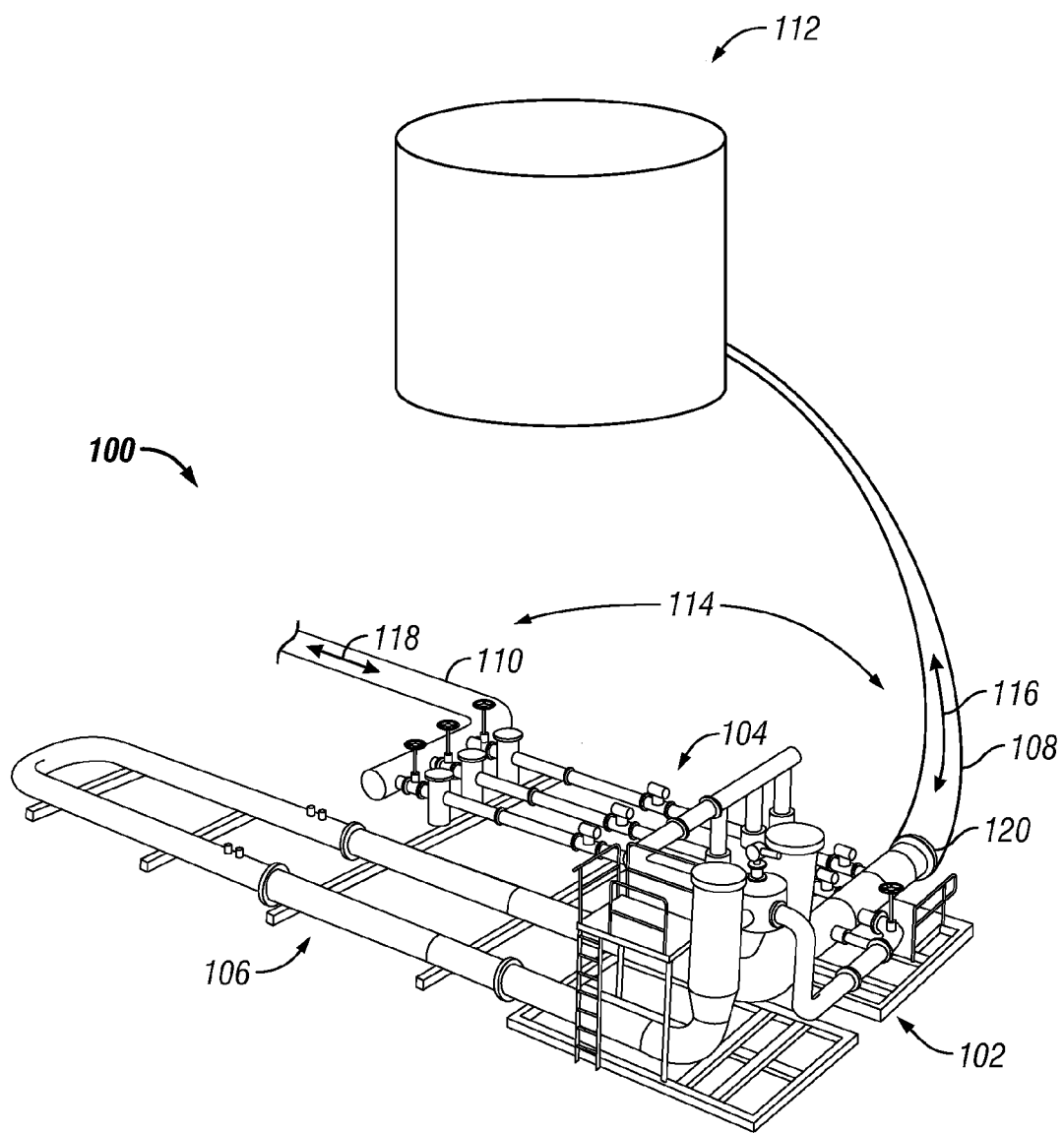
FIG. 1 is a system having a flow meter measurement station in accordance with principles disclosed herein.

In the drawings and description that follow, like parts are typically marked throughout the specification and drawings with the same reference numerals. The drawing figures are not necessarily to scale. Certain features of the invention may be shown exaggerated in scale or in somewhat schematic form and some details of conventional elements may not be shown in the interest of clarity and conciseness. The present disclosure is susceptible to embodiments of different forms. Specific embodiments are described in detail and are shown in the drawings, with the understanding that the present disclosure is to be considered an exemplification of the principles of the disclosure, and is not intended to limit the disclosure to that illustrated and described herein. It is to be fully recognized that the different teachings of the embodiments discussed below may be employed separately or in any suitable combination to produce desired results.

In the following discussion and in the claims, the terms "including" and "comprising" are used in an open-ended fashion, and thus should be interpreted to mean "including, but not limited to . . . ". Unless otherwise specified, any use of any form of the terms "connect", "engage", "couple", "attach", or any other term describing an interaction between elements is not meant to limit the interaction to direct interaction between the elements and may also include indirect interaction between the elements described. The term "fluid" may refer to a liquid or gas and is not solely related to any particular type of fluid such as hydrocarbons. The various characteristics mentioned above, as well as other features and characteristics described in more detail below, will be readily apparent to those skilled in the art upon reading the following detailed description of the embodiments, and by referring to the accompanying drawings.

Flow changes in a pipeline and measurement station can manifest as acoustics that are audible in the pipeline. For example, the flow changes can be caused by pump fluctuations and the related harmonics, down stream back pressure, and gasification of the flowing product. Other phenomena that may cause fluid acoustic changes include fluid velocity changes, fluid density changes, fluid viscosity changes, temperature changes, pressure changes, changes in the particulates or sediments in the pipeline and water content changes. Acoustic change in the pipeline can be used to alert the operator to take action to bring the measurement station back to normal flow state. Therefore, detection of acoustic, sonic or audible signals in the flow lines at the measurement station, and associated apparatus and methods as presented herein, can be used as another vehicle to increase the accuracy and reliability of the measurement station and the resulting custody transfer.

The present disclosure describes collecting acoustic or otherwise audible signals from a delivery line, such as at a measurement station, via audible sensors to detect a change of flow state in the fluid stream. The flow state changes that are detected can be compared to a baseline normal flow state that is previously established. In some embodiments, the process includes identifying flow characteristics in normal state as well as changes to a disturbed state during normal custody transfer at measurement skids. In certain embodiments, commercially purchased sound analysis software and its related highly accurate data acquisition hardware are applied to the measurement skid. In other embodiments, after analysis of normal state flow and unsteady state flow is completed, the metering station Human Machine Interface (HMI) will determine and advise the system operator which changes to make in the operating parameters of the active measurement unit or components to return the fluid flow to steady state. In some embodiments, upon command, the HMI can automatically configure the measurement unit to return the skid to normal state flow.

Referring initially to FIG. 1, a measurement system 100 is shown. A measurement station or skid 102 includes a measurement device or flow meter 104 and a prover 106. The flow meter 104 may be part of a larger measurement unit further having associated equipment and components 114. A first pipeline 108 contains a first fluid stream 116 wherein a fluid is flowing to or from a first container or source 112. The pipeline 108 connects to the flow meter 104. A second pipeline 110 contains a second fluid stream 118 wherein a fluid is flowing to or from a second container or source distant from the skid 102. The skid 102 executes custody transfer measurements. As previously described, the flow characteristics of any of the fluid streams can change during product delivery and operation of the measurement station 102, thereby negatively affecting accurate measurement of the product being delivered.

In one embodiment, first, a baseline of normal flow characteristics is established and recorded. This is done while the measurement station or skid is commissioned, where conditions are controlled and ideal. Areas of flow disturbance during normal operations are identified, the corresponding audible frequency characteristics are measured, and the frequencies are identified as baseline. These flow disturbance areas during normal operating conditions are identified by utilizing known pressure loss characteristics of the device or piping configuration in the fluid flow path. When configuring the measurement station, attention is given to potential changes in the overall flow process both upstream and downstream of the measurement station. Further, the pump, the storage tank and upstream delivery lines are analyzed to determine the probability that these lines will be influenced by flow change. This analysis will determine the placement of the acoustic listening or sensing devices on the delivery line. An acoustic sensing device will be placed on the inlet to the metering unit, and the normal flow state will be identified and documented as the baseline.

Figure 2:
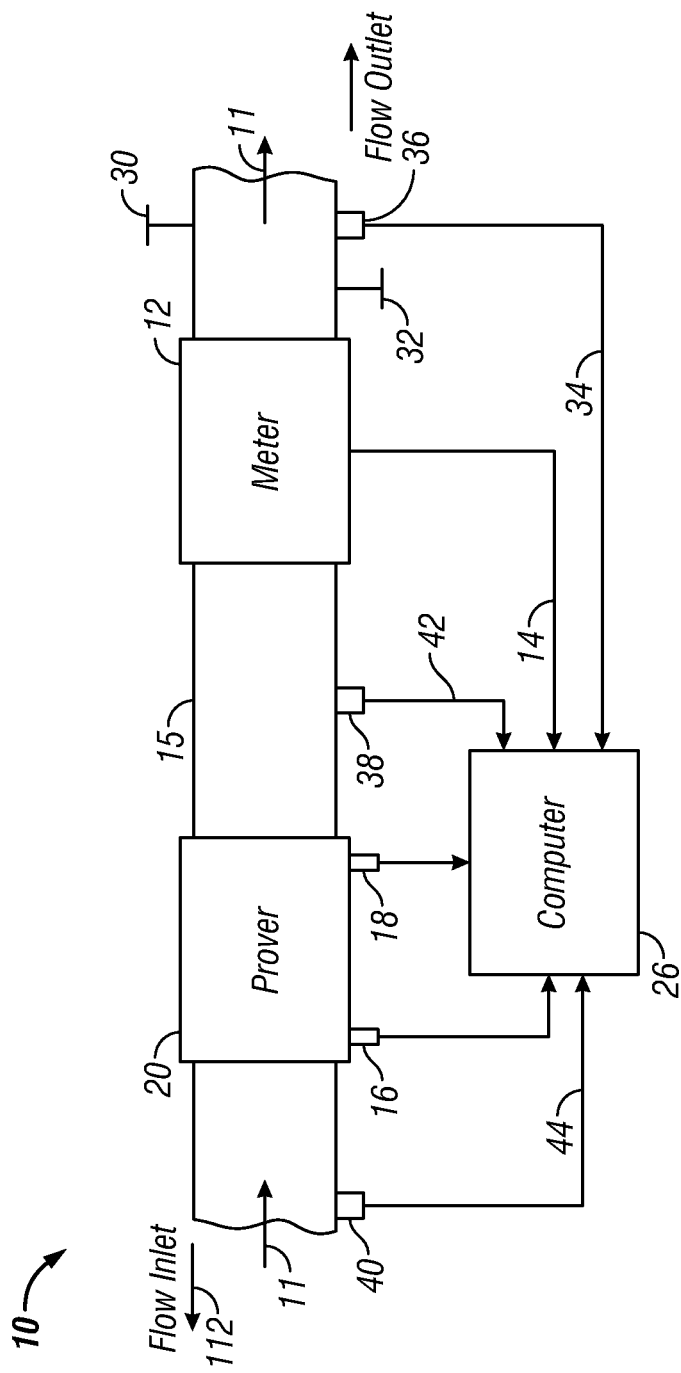
FIG. 2 is a schematic of an alternative system to that of FIG. 1.

In some embodiments, with reference again to FIG. 1, an acoustic sensor may be placed at an inlet 120 of the flow meter 104, at the prover 106, and at the back end of the measurement unit 114. Other combinations and numbers of sensors are also contemplated by the present disclosure. For example, with reference to FIG. 2, a schematic representation of a measurement station 10 includes a pipe 15 receiving a fluid flow 11 from the container 112. The fluid may flow through a prover 20 having sensors 16, 18, then to the flow meter 12 and finally out through the flow control valves 30, 32 to, for example, a refinery. The meter 12 communicates with a computer 26 via line 14. Audible devices may be placed at various locations in the system 10 according to the principles described herein. For example, a microphone 36 is located adjacent the flow control valves 30, 32 and couples to the computer 26 via line 34. Other microphones 38, 40 are located at other locations in the system 10 wherein it is determined that upsets, pressure losses and flow state changes will occur, each microphone communicating with the computer 26 via lines 42, 44, respectively.

The recorded baseline, as previously described, ensures that any changes audibly sensed can be identified as normal or irregular, and the operator can make decisions based on recommendations by the Human Machine Interface (HMI) of the measurement system. In some embodiments, the operator's decision based on the detection of irregularities is to modify the incoming flow to the measurement station, or to reconfigure the measurement station to accommodate the flow state change. In other embodiments, flow changes become apparent within the bounds of the measurement station or downstream of the measurement station, which could affect the overall measurement accuracy of the meter, and, in turn, of the flowing product. Again, the measurement station is pre-examined for areas susceptible to pressure loss in the equipment and the piping components. Areas with potential for flow state changes are outfitted with audible sensors and their baseline frequencies are established. Thus, a normal, baseline audible flow pattern is created including information upstream, midstream and downstream relative to the measurement station. The baseline flow pattern is used to establish the optimized audible flow state from which accurate product measurement can be executed.

Overall normal operation of the pipeline and measurement station system can cause changes to the original audible flow pattern over time, thus deviating from the original baseline while also changing the optimized audible flow state. Such changes during normal operation are identified as normal, and are added to the frequency suite that is identified as normal state. Such changes are normally associated with meter calibration utilizing a prover, or changing overall meter station product throughput by taking meter runs on or offline. Some of these activities are time based, such that irregular flow state can be allowed within a given time period which, if exceeded, can be identified.

After normal flow audible state for the entire measurement station is identified, including normal activities that change the audible characteristics but are identified as optimum for accurate measurement of the station, then audible change which represents non-optimized flow state can be identified, alerted and recommendations can be provided to the operator to bring the flow state back into optimum flow resulting in overall station measurement accuracy. Identifying the location of the audible change through sensor location will dictate the action required, whether it be upstream, at the measurement station, or downstream of the measurement station.

Embodiments herein allow sonic detection of flow state changes at measurement stations. The acoustic signature of the measurement station is identified by the strategic placement of listening devices and using those devices to identify the sound patterns of normal flow which allow optimum measurement. Changes in the sound patterns can be used to identify flow patterns that can reduce accuracy of the measurement unit. Identifying the location where disruption occurs, and making the decisions and actions to bring the measurement station back to optimum flow state will ensure predictable and accurate measurement by the measurement station.

Acoustic and sonic data gathered from in and around a flow meter measurement station is used to adjust flow meter measurements in real time. Though normal operation of a station will produce noise related to flow state changes and pressure loss, the embodiments described herein are primarily adapted for identifying "upsets" relative to the ideal or baseline noise range of the station, and correcting them. Thus, in some embodiments, particular noise characteristics of the station are not as significant as the upsets from the ideal or baseline flow, and the location of such upsets. In addition to the those previously described, pressure losses and upsets that occur outside of the ideal or baseline conditions may include those associated with stripping out a storage tanker, or from changing flow of one product to another, such as from kerosene to gasoline. Further, the flow state upset may indicate deterioration of a component coupled to the flow meter.

In certain embodiments, the measurement station is configured for detecting different fluids flowing in the pipes. The listening devices are adjusted based on the type of product that is flowing and being measured. For example, the flow geometry may be different for each station and its surrounding equipment, and the products in the pipes may have high or low vapor pressures affecting the upsets that can be detected. In some embodiments, such as when a high vapor pressure product (e.g., 400 psi) is flowing and being directed through the station and the flow meter (e.g., liquid propane, butane, gasoline, benzene), more microphones are mounted in and around the station to detect upsets. This is because these products are more volatile and will exhibit more upsets in more locations as compared to their baseline flowing conditions. A lower vapor pressure product (e.g., 10 psi) is more stable and will generally require less microphones.

In some embodiments, calculations are executed to determine where the pressure losses are likely to occur. The geometry of the pipes and valves will affect the calculations. Further, the type of product will affect the calculations. For example, if crude oil is flowing in the pipes, then it is generally known that cavitations only occur downstream of the flow control valves. If, for example, gasoline is flowing in the pipes, there will be additional vapor pressure effects causing upsets in locations other than the flow control valves. Microphones are placed accordingly.

Upon detection of an upset, the computer, processor or HMI will alert the operator of the upset occurrence and its location. In some embodiments, control is then exerted over the measurement station or further parts of the delivery system to correct the upset. For example, back pressure control valves, such as those on the meter or the prover, are adjusted to add backpressure to stabilize the pressure loss related to the upset. In some embodiments, a storage tanker is on one side of the measurement station while a refinery is on the other side, and devices related to these components can also be adjusted to correct upsets.

Figure 3:
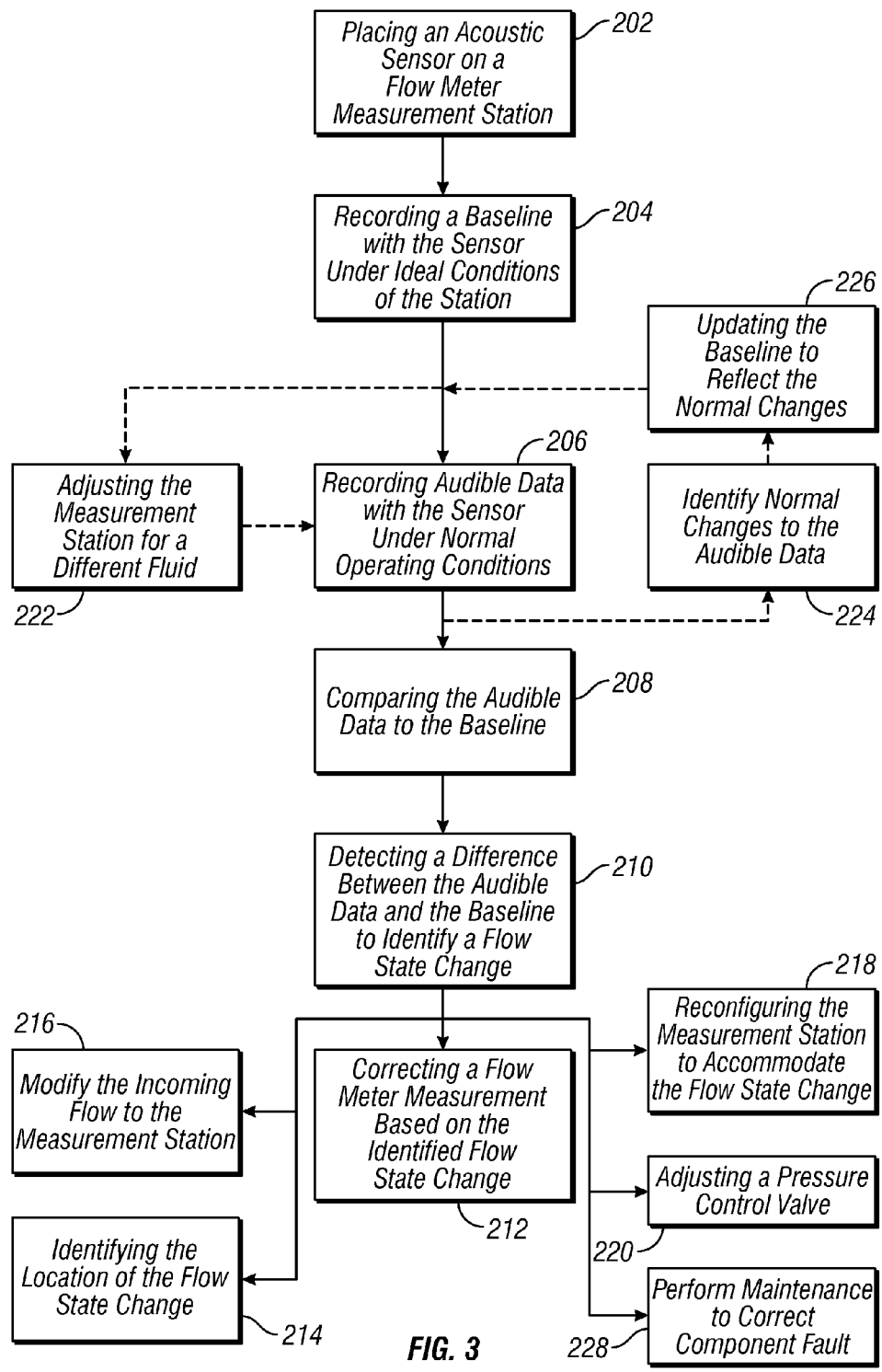
FIG. 3 is a flow diagram of a method in accordance with principles disclosed herein.

Referring now to FIG. 3, several process embodiments in accordance with the principles disclosed herein are captured in a box diagram 200. At 202, one or more acoustic sensors are coupled to a measurement station or the surrounding pipes. At 204, the measurement station is operated under controlled, ideal conditions, such as when the station is being commissioned, to establish and record a baseline of the audible flow pattern. As previously described, the baseline may include pressure losses and flow state changes that are normal and can be accounted for. At 206, the measurement station is operated normally to measure product throughput during custody transfer, and audible data is collected from the sensor or sensors and recorded to establish a real time audible flow pattern. At 208, the real time audible flow pattern is compared to the baseline, and any differences are identified as upsets to the flow state at 210. At 212, a flow meter measurement is corrected based on the identified upset in the flow state. While many corrective actions are covered by the step at 212, exemplary embodiments may include: identifying the location of the flow state change at 214, modifying the incoming flow to the measurement station at 216 (or, alternatively, the outgoing flow to the storage container), reconfiguring the measurement station to accommodate the flow state change at 218, adjusting a pressure control valve at 220, and performing maintenance to correct a component fault at 228.

Still referring to FIG. 3, other embodiments include adjusting the measurement station for a different fluid at 222, such as by tuning the acoustic sensors for a change in fluid type. In some embodiments, the method includes identifying normal changes to the audible data at 224, and updating or adjusting the baseline to include or reflect the normal changes at 226.

While the disclosure is susceptible to various modifications and alternative forms, specific embodiments are shown by way of example in the drawings and description. It should be understood, however, that the drawings and detailed description are not intended to limit the disclosure to the particular form disclosed, but on the contrary, the intention is to cover all modifications, equivalents and alternatives falling within the spirit and scope of the present disclosure.

What is claimed is:

1. A method for audibly detecting a fluid flow state change in a flow meter pipeline comprising:
    placing at least one acoustic sensor in the pipeline coupled to the flow meter;
    collecting audible data from a flowing fluid in the pipeline using the acoustic sensor;
    detecting a flow state change in the flowing fluid by comparing audible data from a first flowing fluid pattern to audible data from a second flowing fluid pattern;
    indicating the flow state change between the first flowing fluid pattern and the second flowing fluid pattern using a computer to correct the measurement of the flow meter based on the flow state change.

2. The method of claim 1 further comprising:
    determining that the flow state change is an upset of a normal fluid flow state; and
    warning an operator of the upset.

3. The method of claim 1 wherein collecting audible data from the first flowing fluid pattern comprises establishing a baseline audible pattern by flowing a controlled fluid through the flow meter under ideal conditions.

4. The method of claim 3 further comprising:
    wherein collecting audible data from the second flowing fluid pattern comprises developing a real time audible pattern by flowing the fluid through the flow meter under normal conditions;
    comparing the baseline audible pattern to the real time audible pattern; and
    identifying a difference between the baseline audible pattern and the real time audible pattern to detect the flow state change.

5. The method of claim 4 further comprising:
    integrating a normal flow state change into the baseline audible pattern; and
    identifying the detected flow state change as an upset in the normal flow state.

6. The method of claim 1 further comprising adjusting at least one of the acoustic sensor, the audible data and the flow state change in response to replacing the flowing fluid with a second fluid.

7. The method of claim 1 further comprising identifying the location of the flow state change.

8. The method of claim 1 further comprising modifying an incoming flow to the flow meter to eliminate the flow state change.

9. The method of claim 1 further comprising adjusting a pressure control valve to eliminate the flow state change.

10. The method of claim 1 further comprising a plurality of acoustic sensors placed at a plurality of positions in the pipeline.

11. The method of claim 1 further comprising identifying deterioration of a component coupled to the flow meter.

12. A method for audibly detecting a fluid flow state change in a flow meter measurement station comprising:

placing at least one acoustic sensor in a pipeline of the flow meter measurement station;

recording a baseline audible pattern of a flowing fluid with the acoustic sensor by flowing a controlled fluid through the flow meter measurement station under ideal conditions;

recording a real time audible pattern of the flowing fluid with the acoustic sensor by flowing a fluid through the flow meter measurement station under normal conditions;

comparing the baseline audible pattern to the real time audible pattern;

detecting a difference between the baseline audible pattern and the real time audible pattern to identify a flow state change;

indicating the flow state change of the flowing fluid using a computer to correct the measurement of the flow meter based on the flow state change.

13. The method of claim 12 further comprising correcting a flow meter measurement using the flow state change to improve the accuracy of the flow meter.

14. The method of claim 12 further comprising reconfiguring the measurement station to accommodate the flow state change.

15. The method of claim 12 further comprising:

integrating the flow state change into an updated baseline audible pattern of the flowing fluid;

detecting a difference between the updated baseline audible pattern and the real time audible pattern to identify an upset in the fluid flow state of the flowing fluid.

16. A system for improving the accuracy of a flow meter by audibly detecting a flow state change comprising:

at least one acoustic sensor mounted on a flow meter skid; and a computer coupled to the acoustic sensor and adapted to collect audible fluid flow data from the acoustic sensor and compare the audible fluid flow data to a pre-determined baseline to detect the flow state change;

wherein the computer is further adapted to correct a measurement of the flow meter using the flow state change.

17. The system of claim 16 wherein the baseline is determined when the flow meter skid is commissioned under ideal conditions.

18. The system of claim 16 wherein the computer is further adapted to warn an operator of an upset in the fluid flow state based on the flow state change.

* * * * *